United States Patent [19]

Masuho et al.

[11] Patent Number: 5,445,960
[45] Date of Patent: Aug. 29, 1995

[54] MONOCLONAL ANTIBODIES SPECIFIC FOR HIV AND HYBRIDOMAS FOR THEIR PRODUCTION

[75] Inventors: Yasuhiko Masuho, Tokyo, Japan; Toru Sugano, Tokyo, Japan; Yoh-Ichi Matsumoto, Tokyo, Japan; Evan M. Hersh, Tucson, Ariz.; Eskild A. Petersen, Tucson, Ariz.; Douglas Lake, Tucson, Ariz.; Takashi Kawamura, Tokyo, Japan

[73] Assignees: The Arizona Board of Regents on behalf of the University of Arizona, Tucson, Ariz.; Teijin Limited, Osaka, Japan

[21] Appl. No.: 65,522

[22] Filed: May 24, 1993

Related U.S. Application Data

[63] Continuation of Ser. No. 342,899, Apr. 25, 1989, abandoned, which is a continuation-in-part of Ser. No. 176,159, Mar. 31, 1988, Pat. No. 5,298,419.

[51] Int. Cl.$^6$ .................. C12N 5/24; C07K 15/28
[52] U.S. Cl. .................... 435/240.27; 435/70.21; 435/172.2; 530/388.15; 530/388.35; 530/389.4; 424/148.1
[58] Field of Search ............ 424/85.8, 86, 85.91; 530/388.15, 388.35, 389.4; 435/70.21, 172.2, 240.27

[56] References Cited

PUBLICATIONS

Desgranges (Apr. 23, 1988) The Lancet, pp. 935–936.
Dreesman, J. Cell. Biochem (Mar. 29–May 1, 1987) Supp 11D Abs. PO14, p. 34.
Kennedy et al., J. Biol Chem. (Apr. 1987) 262(12): 5769–74.
Lasky et al, Science (Jul. 1986) 233: 209–222.
Roitt et al., Chapter 5 in Immunology (1985) 5.1–5.10. Roitt, Brostoff & Male (eds) Gower Medical Publishing, N.Y.
Foung et al., Appendix—Chp 6 in Human Hybridomas and Monoclonal Antibodies (1985) Engleman, Foung, Larrick & Raubitshok (ed) Plenum Press, pp. 437–440.
Banapour et al., III International Conference on AIDS, Jun. 1–5, 1987, Washington, D.C., Abstract #TP. 114 on p. 81.
McDougal et al., J. Cellular Biochemistry (Mar. 29–May 1, 1987) Suppl 11D, Abstract PO18, p. 36, Alan R. Liss Inc, N.Y.
Chanh et al., Eur. J. Immunol., (1986) 16: 1465–1468.
Larrick et al., Chp 9 in Human Hybridomas and Monoclonal Antibodies (1985) Engleman, Foung, Larrick & Raubitshek (ed.) Plenum Press, pp. 149–165.
*Journal of Immunological Methods*, (1988), vol. 106, pp. 257–265, "The High Efficiency, Human B Cell Immortalizing Heteromyeloma CB-F7", R. Grunow et al.
*Monoclonal Antibody—Production Techniques and Applications*, (1987), vol. 33, pp. 51–63, "Mouse-Human Myeloma Partners For The Production . . . " B. Brodeur et al.
*Biochemical and Biophysical Research Communications*, (1988), vol. 155, pp. 1105–1112, "Human Monoclonal Antibody Against Glycoproteins . . . " T. Sugano et al.
*Journal of Immunology*, (1988), vol. 140, pp. 941–943, "Human Monoclonal Antibody Directed Agains gag Gene Products of the Human . . . " L. Evans et al.
*Journal of Immunology*, (1987), vol. 139, pp. 4027–4033, "Characterization and Epitope Mapping of a Human Monoclonal Antibody Reactive With . . . " B. Banapour et al.
*Journal of Clinical Microbiology*, (1987), vol. 25, pp. 845–848, "Monoclonal Antibodies To gp110 and gp41 of Human Immunodeficiency Virus". Gosting et al.

(List continued on next page.)

Primary Examiner—David L. Lacey
Assistant Examiner—Robert D. Budens
Attorney, Agent, or Firm—Oblon, Spivak, McClelland, Maier & Neustadt

[57] ABSTRACT

Human IgG1 monoclonal antibodies are produced by hybridoma ATCC HB10074 and bind to gp120 of HIV.

3 Claims, 7 Drawing Sheets

PUBLICATIONS

*Chemical Abstracts*, 108:54050h, Characterization and epitope mapping of a human monoclonal antibody reactive with the envelope glycoprotein of human immunodeficiency virus. Banapour

*Chemical Abstracts*, 108:166098m, Immortalized cells which produce tissue-specific products and their formations. Foung.

*Chemical Abstracts*, 110:55817s, Immortalized virus-specific tissue cells, their preparation and uses. Foung.

*Chemical Abstracts*, 112:19784m, CD4 antigen-based antireceptor peptides inhibit infectivity of human immunodeficiency virus in vitro at multiple stages of the viral life cycle. Nara.

*Chemical Abstracts*, 105:207285d, Induction of CD4-dependent cell fusion by the HTLV-III/LAV envelope glycoprotein. Lifson.

*Chemical Abstracts*, 106:46942u, Role of envelope glycoprotein carbohydrate in human immunodeficiency virus (HIV) infectivity and virus-induced cell fusion. Lifson.

A: AIDS PATIENT'S SERUM
B: HEALTHY DONOR SERUM
C: NO. 86
D: " SUBCLONE 1.
E: " SUBCLONE 2.
F: " SUBCLONE 3.
G: " SUBCLONE 4.
H: " NO. 1
I: " 81-1

|  | PRETREATMENT OF ANTIGEN | | SAMPLE BUFFER USED FOR SDS PAGE | MCA USED FOR RIPA |
|---|---|---|---|---|
| LANE 1 | −SH | (INFECTED) | +SH (+2%2ME)* | S1-1 |
| 2 | +20mMDTT,30min | ( " ) | " | " |
| 3 | " ,60min | ( " ) | " | " |
| 4 | +100mMDTT,30min | ( " ) | " | " |
| 5 | " ,60min | ( " ) | " | " |
| 6 | −SH | ( " ) | " | PATIENT'S SERUM |
| 7 | +20mMDTT,30min | ( " ) | " | " |
| 8 | " ,60min | ( " ) | " | " |
| 9 | +100mMDTT,30min | ( " ) | " | " |
| 10 | " ,60min | ( " ) | " | " |
| 11 | MOLECULAR WEIGHT MARKER | | | |

* 2ME: 2 MERCAPTOETHANOL

| | PRETREATMENT OF ANTIGEN | SAMPLE BUFFER USED FOR SDS PAGE | | MCA USED FOR RIPA |
|---|---|---|---|---|
| LANE 1 | −SH | (MOCK INFECTED) | +SH (+2%2ME) | S1-1 |
| 2 | " | (INFECTED) | " | " |
| 3 | " | (MOCK INFECTED) | " | 110-13 |
| 4 | " | (INFECTED) | " | " |
| 5 | MOLECULAR WEIGHT MARKER | | | |

| | PRETREATMENT OF ANTIGEN | SAMPLE BUFFER USED FOR SDS PAGE | | MCA USED FOR RIPA |
|---|---|---|---|---|
| LANE 1 | -SH | (MOCK INFECTED) | -SH | S1-1 |
| 2 | ″ | (INFECTED) | ″ | ″ |
| 3 | ″ | (MOCK INFECTED) | ″ | PATIENT'S SERUM |
| 4 | ″ | (INFECTED) | ″ | ″ |

MONOCLONAL ANTIBODIES SPECIFIC FOR HIV AND HYBRIDOMAS FOR THEIR PRODUCTION

This application is a continuation of application Ser. No. 07/342,899 filed Apr. 25, 1989, now abandoned, which is a continuation-in-part of application Ser. No. 07/176,159 filed Mar. 31, 1988, now U.S. Pat. No. 5,298,419.

BACKGROUND OF THE INVENTION

1. Field of the Invention

The present invention relates to human monoclonal antibodies (abbreviated as MCAs hereinafter) specific for the human immunodeficiency virus, and the hybridomas which produce said MCAs. The objective of this invention is to provide human MCAs which are specific for HIV and which will be useful in the diagnosis, prevention and therapy of HIV infection.

2. Discussion of the Background

HIV is a virus which primarily infects helper T lymphocytes and brings about extreme immunological failure by destroying those cells, thereby causing AIDS (acquired immunodeficiency syndrome). In the early stage of HIV infection, some patients develop symptoms which resemble those of infectious mononucleosis, i.e., fever, fatigue, headache, etc. Subsequently, although the patient becomes asymptomatic, he/she becomes a carrier of anti-HIV antibodies in the blood. Then, after a latent period lasting a number of years, the patient develops AIDS-related complex (ARC). ARC patients exhibit various symptoms such as systemic swelling of lymph nodes, fever, general fatigue, weight loss, decreased platelet and lymphocyte levels, etc. As the disease progresses, the patient becomes susceptible to and develops Kaposi's sarcoma and various opportunistic infections such as *Pneumocystis-carinii* pneumonia, fungal infections, cytomegalovirusinfection, etc., which end in death. The most striking characteristics of AIDS are the decrease in helper T lymphocytes (T4), and a steady decrease in the ratio of T4 to suppressor T lymphocytes (T8), i.e., T4/T8, as the disease progresses.

AIDS was first reported in the United States of America in 1981, and it has been estimated that today there are more than 20,000 AIDS patients in the USA alone. Carriers of the virus have been estimated to number one million persons in the USA. In addition to the USA, there are also many AIDS victims in Africa and Europe, and there is a huge amount of research being carried out today on methods for the diagnosis, prevention and treatment of AIDS.

HIV, the causative agent of AIDS, is a retrovirus. This virus has been shown to be composed of RNA consisting of about 9,700 base pairs, three gag proteins (having molecular weights of 55,000, 24,000 and 17,000daltons), a reverse transcriptase (molecular weights of 66,000 and 51,000 daltons have been detected), three glycoproteins (two molecules having molecular weights of 120,000 and 41,000 daltons, and their precursor, a molecule with a molecular weight of 160,000 daltons; these glycoproteins are hereinafter abbreviated as gp120, gp41 and gp160) which comprise the envelope, and other components. Especially from the viewpoints of viral infection and the prevention thereof, the envelope, which is exposed as the surface of HIV, carries particular importance. As a result of proteolysis, gp160 is cleaved into gp120 and gp41. Gp41 is a transmembrane protein which is incorporated into the lipid bilayer of the viral envelope, while gp120 is exposed on the outside of the envelope and some of it is released from the virus. Both gp41 and gp120 possess many sugar-binding sites, and about half of the gp120 molecule is comprised of sugars. The gp120 molecule binds to, or near to, the CD4 antigens which exist on the cell surface of helper T cells, etc., and in addition to bringing about infection of the cells by the virus, gp120 possesses activity which results in the syncytium formation in the cells.

For example, M. Robert-Guroff et al. (J. Immunol. 138: 3731, 1987) reported that the progression of the disease was slower in patients whose blood contained viral-neutratizing antibodies in comparison with patients not having such antibodies. In addition, it has been reported that the neutralizing antibodies in the blood of AIDS patients bind to gp120 (L.A. Lasky et al.: Science 233: 209, 1986; and T. J. Matthew et al.: Proc. Natl. Acad. Sci. USA 83: 9709, 1986).

Even more important there are reports of passive immunotherapy with high titer anti p-24 plasma in patients with HIV infection. This has cleared antigenemia and improved clinical prognosis. (A. Karpas et al.: Proc. Natl. Sci. USA 85: 9234, 1988; and G. G. Jackson: Lancet, 2, 647, 1988).

In light of the above background information regarding HIV and AIDS, it is obvious that neutralizing antibodies specific for viral antigens exposed on the surface of the virus or infected cells have great significance in the prevention and/or treatment of said infection.

A number of research groups have already reported successful development of mouse MCA specific for gp120. For example, T.C. Chanh et al. (Eur. J. Immunol. 16: 1465, 1986) reported that they chemically synthesized a portion of the peptide chain of gp120 and then prepared an MCA specific for that synthetic peptide. They employed that MCA in the indirect fluorescent antibody technique and reported that they were able to detect HIV infection with greater sensitivity than was possible with the reverse transcriptase determination technique. In addition, Gosting et al. (J. Clin. Microbiol.: 25, 845, 1987) reported that they solubilized HIV viral antigens, adsorbed them to a column of lentil lectin-Sepharose 4B, collected the glycoprotein fraction thereof and used it to immunize mice, and succeeded in producing anti-gp120 mouse MCA and anti-gp41 mouse MCA. Matsushita et al. (Medical Immunol. 14: 307, 1987) also reported-achieving viral neutralization with an anti-gp120 mouse MCA. These MCAs are useful in the diagnosis of HIV infection, but they are unfortunately unsuited for the tasks of prevention of HIV infection and treatment of established disease (ARC and AIDS). The reason for this is that, since those MCAs are mouse proteins, they are recognized as foreign by the human immune system if they are administered to the human body. As a result, not only would the MCA activity be inhibited by the anti-mouse MCA antibodies that would be produced by the human immune system, but anaphylactic side effects would also occur. Therefore, it is clear that, for the prevention and treatment of HIV infection in man, it is necessary to develop a human-origin MCA, not a mouse-origin MCA.

In general, human-origin anti-HIV MCAs can be produced by (1) hybridomas obtained by fusion of human B lymphocytes having the ability to produce antibodies specific for HIV and cells of established lymphoid cell lines such as myeloma cells, and (2) lymphoblastoid cells obtained by Epstein-Barr (EB) virus-induced transformation of human B lymphocytes having the ability to produce antibodies specific for HIV. From about 1980 up to the present time, much research has been carried out on the production of human MCAs, but none of those efforts have led to an established method such as in the case of mouse MCAs because each of the approaches described above has its own special problems.

In 1987, there were two reports concerning human MCAs specific for HIV. One was by L. Evans et al. (Proceedings of the Third Congress on AIDS, TP130, 1987). They reported that they employed EB virus to transform lymphocytes from HIV-infected patients and obtained a human MCA which reacted with gag proteins having molecular weights of 55, 41 and 25 kilodaltons. That human MCA belonged to the IgG4 subclass, and it did not neutralize HIV. The second report was by B. Banapour et al. (ibid, TP114); they also employed EB virus to transform lymphocytes from anti-HIV antibody-positive subjects, fused the transformed cells with heteromyeloma cells, and obtained a human MCA which reacted with gp41. This MCA was IgG, but the subclass was not reported. This MCA also did not show HIV-neutralizing activity. Thus, in both of those reports, transformation by EB virus was employed. This technique, because it is very efficient at achieving immortalization of human B lymphocytes, is far superior to the cell fusion method. Nevertheless, the obtained lymphoblastoid cell lines produce EB virus, or even if they do not produce the virus particles, they contain the EB viral DNA which carries the potential for production of the virus. EB virus has the ability to transform lymphocytes, which means that this virus has tumorigenicity. Therefore, there is worry concerning the safety of using this EB virus transformation technique to produce a drug product for administration to humans.

It is also known that lymphoblastoid cells resulting from transformation of lymphocytes by EB virus can be further infected by HIV, and there is thus the fear that a cell line producing human MCA might be infected by both EB virus and HIV. In addition, the antibody production by lymphoblastoid cell lines presents some disadvantages in view of the facts that it is usually lower and also less stable than the level of production by hybridomas. The reason that Banapour et al. performed additional cell fusion of lymphoblastoid cell lines was to attempt to improve the antibody producing ability of those cell lines.

Accordingly, as seen above, if the immortalization of human B lymphocytes could be achieved with greater efficiency by cell fusion and if a hybridoma having the ability to produce human MCA specific for HIV could be obtained, then the resultant hybridoma would be very desirable on the basis of its having high productivity of an MCA which would moreover be safe for use as a drug.

With regard to the subclass which would be the most desirable for human MCAs, it is evident that it would be advantageous for the antibody to be of a subclass which possesses the ability to activate complement and the ability to bind to the Fc receptors on macrophages and lymphocytes. It has been demonstrated that activation of complement by the classical pathway can be achieved by the IgG1 and IgG3 subclasses, whereas IgG2 and IgG4 cannot carry out this activation (J. L. Winkelhake: Immunochem. 15: 695, 1978). Furthermore, it has also been shown that the IgG1 and IgG3 subclasses have a strong affinity for the Fc receptors of monocytes (Cosio et al.: Immuno. 44: 773, 1981). Therefore, for the objective of prevention of infection of cells, it is clear that the IgG1 and IgG3 subclasses are desirable.

However, another consideration is necessary: that of purification of the produced human MCA. Affinity chromatography using protein A can be effective for the purification of MCAs, and since IgG1 binds to protein A whereas IgG3 does not, it is clear that the IgG1 subclass of human MCA would be the most desirable subclass from the viewpoint of ease of purification.

SUMMARY OF THE INVENTION

The inventors of the present invention, as a result of carrying out vigorous research aimed at obtaining an anti-HIV human MCA and employing a method involving fusion of mouse myeloma cells and lymphocytes from the lymph nodes or spleen of HIV-seropositive donors, succeeded in obtaining a hybridoma which produces a human MCA (IgG1 subclass) specific for gp121, and a hybridoma which produces a human MCA (IgG1 subclass) reacting with both gp120 and gp41. They also succeeded in culturing those hybridomas and/or cell lines originating from those hybridomas and were able to collect the anti-HIV human MCAs from the supernatants of those cell cultures.

That is, the present invention consists of human monoclonal antibodies which are specific for HIV and belong to the IgG1 subclass, specifically an IgG1 antibody which binds with gp120 of HIV, and IgG1 antibody which binds with both gp120 and gp41 of HIV. In addition, this invention consists of the hybridomas which produce those human monoclonal antibodies and were formed by fusion between human lymphocytes and mouse myeloma cells. These hybridomas have been registered with the American Type Culture collection, 12301 Parklawn Drive, Rockville, Md. 20851USA as deposition numbers HB9669, HB9670 and HB10074 (Sl-1). In addition, another aspect of this invention is the method by which the inventors succeeded in efficiently forming those hybridomas, a method in which human lymphocytes were first treated with complement and anti-human T-lymphocyte mouse MCA or AET treated SRBC and Ficoll and then the treated human lymphocytes were fused with mouse myeloma cells.

BRIEF DESCRIPTION OF THE DRAWINGS

A more complete appreciation of the invention and many of the attendant advantages thereof will be readily obtained as the same become better understood by reference to the following detailed description when considered in connection with the accompanying drawings, wherein.

BEST MODE OF CARRYING OUT THE INVENTION

Figure 1:
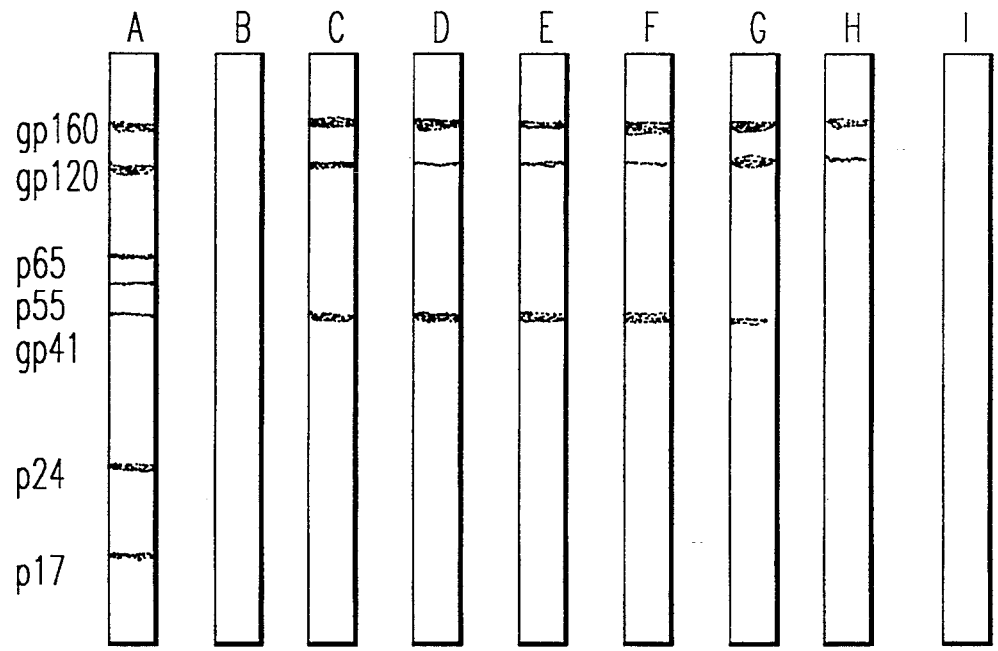
FIG. 1 illustrates the results of a Western blot analysis to determine the viral antigens recognized by the MCAs.

The human lymphocytes employed in the method of this invention can be obtained from the spleen, lymph nodes, peripheral blood, bone marrow, tonsils, adenoids, etc., of seropositive donors. To achieve the objective of this invention, use can be made of lymphocytes from any of those sources, but it is most desirable that they be obtained from the lymph nodes, spleen or tonsils of seropositive donors or patients with lymphadenopathy.

As the mouse myeloma cells, it is advantageous to employ a cell line which is resistant to 8-azaguanine, and the following are some of the publicly-known cell lines from BALB/C mice: P3x65Ag8, P3-NS1/1-Ag4-1, P3x63AgU1, SP2/OAg14, P3x63Ag8.6.5.3, MPCll-45.6.TG1.7 and SP-1.

In the method of this invention, prior to the fusion of the human lymphocytes and the mouse myeloma cells, it is desirable to treat the human lymphocytes with complement and an anti-human T-lymphocyte mouse MCA (e.g., OKT3, a product of Ortho Diagnostics Co., Ltd.) or to treat the human lymphocytes with AET (Aminoethylisothiouranium Bromide Hydrobromide) treated SRBC (sheep red blood cells) and Ficoll so as to eliminate the human T-lymphocytes. In the actual performance of the method of this invention, for example, a fixed lymphatic tissue is surgically excised from a seropositive human donor and gently dissected with scissors and a scalpel to obtain a liquid containing suspended cells. Then, to remove T-cells from these suspended cells, the following two methods were used:

(1) This suspension is then layered onto a Ficoll-Paque solution, and the lymphocytes are separated and harvested by centrifugation. Then, the lymphocytes are treated with 0.5 ml of fresh serum as the source of complement and 1.0 ml of an anti-human T-lymphocyte mouse MCA to destroy the T-lymphocytes and resultant B-lymphocytes are? harvested by centrifugation.

(2) This suspension is mixed with AET treated SRBC and then layered onto a Ficoll-Paque solution and B-lymphocytes are separated and harvested by centrifugation. If B-lymphocytes were used instead of nontreated lymphocytes, the hybridoma formation is increased.

The thus-obtained human B-lymphocytes are then fused with mouse myeloma cells. The general conditions for cell fusion and culture of hybridomas are already known, but the inventors nevertheless carried out vigorous research to determine the most desirable combinations for achieving formation of hybridomas and propagation of them and as a result were able to achieve formation of one hybridoma for every $10^4$ lymphocytes treated by the method of the invention.

Those conditions were determined to be as follows. For example, lymphocytes and mouse myeloma cells are mixed at a ratio of 10:1 to 1:100, preferably 1 to 1:10, a suitable solution for cell fusion, such as RPMI 1640 containing ca. 35% polyethyleneglycol (molecular weight: about 1,000-6,000) and ca. 7.5% dimethylsulfoxide is added, this cell suspension is stirred for one to several minutes at a temperature in the ambient to 37° C. range, this suspension is gradually diluted and then washed with RPMI 1640 containing 10% fetal calf serum (FCS), and finally it is adjusted with HAT (hypoxanthine-aminopterin-thymidine) selective culture solution to give a cell density of $1-5\times10^5$/ml. Mouse peritoneal exudate cells are added to a 96-well plate as a feeder layer, and the culture solution is removed immediately before the fused cells are introduced by dispensing 0.2 ml aliquots of the suspension into the wells of the plate. These are then cultured for 2-3 weeks at 35-38° C. in humidified air containing 5% $CO_2$. Only hybridoma cells are present in the HAT culture solution, since the 8-azaguanineresistant myeloma cells and cells arising from fusion of myeloma cells cannot survive in the HAT solution (unfused antibody-producing cells die within a few days).

After the culture of the hybridomas in the 96-well plates, the antibody titer of the culture fluid of each well containing cells is determined by the enzyme-linked immunosorbant assay (ELISA) technique, and only hybridomas which produce the desired antibodies are selected. Cells of each selected hybridoma are collected, cloning is performed by the limiting dilution method, and subclones which stably produce an MCA are established.. Then those hybridomas are further investigated by analyzing the antigens recognized by their produced MCAs by the Western blot analysis and/or Radioimmunoprecipitation analysis technique, and investigating the ability of the produced MCAs to bind to the surface of HIV-infected cells, and those hybridomas which are producing an MCA which binds to gp120 or gp160 and which is able to bind to the surface of infected cells are finally selected.

The mouse-human hybridomas which were obtained by the method of this invention as described above and which produce anti-HIV human MCAs can be preserved by freezing. If these hybridoma cell lines and/or cell lines derived from them are cultured on a large scale by an appropriate method, it is possible to obtain from the culture supernatant the human MCAs which are the objective of the present invention. In addition, these hybridomas are transplanted into animals to form tumors, the produced human MCA can be obtained from the ascites or the serum of the animals.

The anti-HIV human MCAs which have been obtained by the methods described above have been found to have the following characteristics. (1) In ELISA using fixed viral antigens obtained from HIV-infected cells, the MCAs were positive for binding, but they were negative for binding in ELISA using a plastic coated with substances obtained from uninfected cells by the same technique. (2) Since HIV is composed of many antigenic substances, the Western blot analysis technique and/or RIPA technique was applied to determine the nature of the structural components to which the human MCAs obtained in this invention bind. It was thus found that one of the human MCAs binds to a molecules having molecular weights of 120K and 160K (160K is the precursor of 120K and 41K molecules). The second MCA was found to bind to molecules having molecular weights of 41K, 120K and 160K. (3) The MCAs were investigated to determine whether or not they bind to the surface of HIV-infected cells. After the human MCA was reacted with unfixed HIV-infected cells, fluorescein-labeled antibody to human IgG was allowed to react, and strong fluorescence was observed on the surface of the infected cells. Therefore, it was learned that all of the human MCAs of this invention bind to the surface of infected cells. (4) Human IgG is known to have four subclasses, i.e., IgG1, IgG2, IgG3 and IgG4, with each subclass having its own characteristic biological activities. Each of the anti-HIV human MCAs obtained in this invention was thus investigated for its subclass using a specific animal antiserum, and it was found that all of the MCAs of this invention belong to the IgG1 subclass.

Experimental Example 1

A. Cell Fusion.

1. Collection of Lymphocytes

A lymph node which was surgically excised from an ARC patient was finely minced using scissors and a scalpel. Cells therefrom were suspended in medium A (RPMI 1640 containing 10% fetal calf serum (FCS), 2 mM glutamine, 1 mM sodium pyruvate, 20 $\mu$g/ml L-serine, 0.05 $\mu$/ml human insulin and 80 $\mu$g/ml gentamicin sulfate). This cell suspension was layered onto a Ficoll-Paque solution and centrifuged at 1,500 rpm for 20 min. The cells which collected on the top of the Ficoll-Paque solution were harvested, centrifugally washed once with phosphate-buffered saline (PBS) and twice with RPMI 1640. Finally, the cells were resuspended in RPMI 1640 to a concentration of $1 \times 10^7$ cells/ml.

2. Treatment of Lymphocytes

To reduce the amount of cell fusion that would take place with T-lymphocytes, the T-lymphocytes in the lymphocyte suspension were eliminated by either of the following two methods.

(1) OKT3 (Ortho Diagnostics Co., Ltd.) was added to the above-mentioned cell suspension to give a final 200-fold dilution. After reacting at 4° C. for 60 minutes, the cells were precipitated by centrifugation (1,500 rpm for 5 min). Next, baby rabbit complement was diluted 3-fold (with RPMI 1640) and added to the cell pellet to obtain a suspension, which was then reacted at 37° C. for 60 min. Then this cell suspension was twice subjected to centrifugal washing.

(2) The same volume of $1 \times 10^8$ AET treated SRBC suspension in medium A was added to the above-mentioned cell suspension. After gently mixing this at room temperature for 5 minutes, the cells were precipitated by centrifugation at 1000 rpm for 5 minutes. The cell pellet was incubated at room temperature for 20 minutes, then gently suspended, and layered onto. Ficoll-Hypaque. After centrifugation at 1500 rpm for 20 minutes, the B-lymphocyte fraction was collected from the interface layer of the medium and the Ficoll-Hypaque and subjected to centrifugal washing.

3. Cell Fusion

The OKT3-treated or AET rosette treated lymphocytes or untreated lymphocytes were each mixed with mouse myeloma P3U1 cells (both cell populations were $3 \times 10^7$ cells) in RPMI 1640 medium. These cell mixtures were then precipitated by centrifugation (1,600 rpm, 5 min). The supernatant was discarded, and the cell pellet was broken up by tapping the tube. Then 1 ml of polyethylene glycol solution (35% v/v polyethylene glycol No. 1000 and 7.5% v/v dimethylsulfoxide in RPMI 1640) was slowly added to the tube, and this was allowed to stand for one minute at room temperature. Next, 2 ml of RPMI 1640 was added, and it was allowed to stand for one minute; another 2 ml of RPMI 1640 was added, and it was allowed to stand for 2 minutes. Then 4 ml of HAT medium (95 $\mu$M hypoxanthine, 5.4 $\mu$M aminopterin, and 16 $\mu$M thymidine in medium A) was added, and the mixture was allowed to stand for 2 minutes; another 8 ml of HAT medium was added and the mixture was allowed to stand for 2 minutes; an additional 24 ml of HAT medium was added and the mixture was allowed to stand at 37° C. for 30 minutes. Finally, the total volume was made up to between 75 and 150 ml by the addition of HAT medium.

Aliquots of approximately 200 $\mu$l were seeded into the wells of a 96-well flat culture plate. This culture plate had been pretreated by seeding ICR mouse (male) peritoneal exudate cells at $2 \times 10^4$ cells/well; immediately prior to the seeding of the fused cells, the culture fluid was removed from the wells. This culture plate was then incubated at 37° C. in a $CO_2$ incubator. Once per week, half of the culture medium in each well was replaced by HT medium (HAT medium from which aminopterin had been left out), and the incubation was continued until hybridoma colonies became apparent.

4. Cloning

At the time when hybridoma colonies became apparent, each of the culture fluids was treated for the presence of antibody activity directed at HIV. The hybridomas of colonies which were found to be producing HIV-specific antibodies were then cloned. First, 96-well flat plates were seeded with only mouse peritoneal exudate cells at $2 \times 10^4$ cells/well. Then, at various times from one hour to one day after the seeding, the culture medium was removed and the hybridomas were seeded into 96 wells each at 10 cells/well. For the first cloning, HT medium was employed, while medium A was used for the second cloning. After 2–3 weeks of culture, the antibody activity was determined, and positive clones were picked up.

B. ELISA (Enzyme-Linked Immunosorbent Assay)

1. Viral Antigens
   a. HTLV-III (human lymphotropic virus type III) antigen (Bionetics Laboratory Products Co., Ltd.)
   b. CR10/N1T Antigens CR10/N1T is a cell line which was established by creating a persistent infection of CEM cells with the N1strain of HIV. The viral antigens were partially purified from this CR10 cell line. In brief, CR10/N1T cells were washed 3 times with PBS and then frozen at $-70°$ C. At the time of use, the frozen cells were thawed, and $10^8$ cells were suspended in 9 ml of distilled water; this cell suspension was vigorously agitated for one minute using a Vortex blender. This was then centrifuged for 10 minutes at 2,800 rpm, and the supernatant was collected. One ml of 10-fold concentrated PBS was next added to the supernatant, centrifugation was performed at $15,000 \times g$ for 30 min, and the pellet was collected. The pellet was resuspended in 5 ml of PBS, sonicated 4 times for 15 sec each while chilling in ice and allowed to stand for a further 30 minutes while chilling in ice; the supernatant was then collected. The supernatant was subjected to ultracentrifugation at $100,000 \times g$ for one hour, and the supernatant was employed as the viral antigen preparation. As the negative control, an antigen preparation was obtained by treating CEM cells (uninfected by HIV) in the same manner.

2. Antigen-Coated Plates

HTLV-III antigen (1 $\mu$g/ml), CR10/N1T antigens (20–25 $\mu$g/ml) and CEM antigens (20–25 $\mu$g/ml) were each dispensed in aliquots of 50 $\mu$l to the wells of separate microtiter plates (Coster, No. 3912), and the plates were then allowed to stand at 37° C. for 60 min. The plates were then washed twice with HBSS-BSA (Hank's balanced salt solution, 0.5% bovine serum albumin and 0.1% NAN3), PBS (Ca++, Mg++) containing 3% BSA was dispensed at 125 μl/well, and the plates were allowed to stand at 37° C. for 60 min and then at 4° C. overnight to carry out blocking.

3. ELISA

The antigen-coated plates were washed twice with HBSS-BSA, and then 50 μl of each of the heated (56° C. for 60 minutes) hybridoma culture fluids was added. After letting these react at room temperature for 60 minutes, the plates were again washed twice with HBSS-BSA. Then 50 μl of alkaline phosphatase-conjugated goat antibody to human IgG (diluted 1000×x; Tago Inc.) were added, and reaction was again allowed to take place at room temperature for 60 minutes before the plates were washed 4 times with HBSS-BSA. Next, 100 μl of 0.05 M carbonate buffer containing 1 mg/ml p-nitrophenylphosphate and 1 mM $MgCl_{12}$, pH 9.5, was added to each well, and the plates were reacted at room temperature for 60 minutes or overnight. Finally, the optical density was measured at 405 nm using an ELISA Reader (Titertech Inc.).

C. Experimental Results

1. Lymph. node cells from Patient A were compared with and without OKT3 treatment.

TABLE 1

Generation of Hybridomas Producing IgG Antibodies to HIV*

| Treatment | Number of Anti-HIV IgG-Positive Wells | | |
|---|---|---|---|
| | High O.D.** | Medium O.D. | Low O.D. |
| − OKT3 | 3 | 2 | 1 |
| + OKT3 | 6 | 5 | 6 |

*Indicates wells containing hybridomas which produce IgG that reacts with CR10/N1T antigens but not with negative control (CEM antigens).
**"High" means that the optical density at 405 nm was larger than 1.0, while "Medium" indicates the 0.4–1.0 range and "Low" represents the 0.2–0.3 range. Therefore, more hybridomas producing IgG antibodies to HIV were generated in the case of the lymphocytes which were treated with complement and anti-lymphocyte antibody.

2. As reported above, hybridomas were obtained by fusion of mouse myeloma cells with OKT3-treated lymphocytes from the lymph nodes of patients with ARC, those hybridomas were cloned, and the inventors successfully established hybridomas No. 86 (aTCC No. HB9669) and No. 1, (aTCC No. HB9670which stably produce MCAs. On the other hand, hybridoma Sl-1 (aTCC No. HB10074) which stably produces MCA was obtained by fusion of mouse myeloma cells with AET rosette-treated lymphocytes from the spleen of patients with ARC. In ELISA, the MCAs produced by hybridomas No. 86, No. 1, and Sl-1 reacted with HTLV-III antigen and CR10/N1T antigens but not with CEM antigens. The MCA production rates were 10 μg/$10^6$ cells/day in the case of No.86, 20 μg/$10^6$ cells/days in the case of No. 1, and 5 μg/$10^6$ cells/day in the case of Sl-1.

Experimental Example 2

A. Purification of MCAs

The Culture fluids (1.5–2 liters) of hybridomas No. 86, No. 1, and Sl-1 were used as the starting materials. Ammonium sulfate was added to the culture fluids to 50% saturation, and the resultant protein precipitates were collected by centrifugation at 10,000 rpm for 30 min. The precipitates were then dissolved in a suitable volume of PBS, followed by dialysis against PBS. The dialyzed solution was next applied to a protein A-Sepharose column bed (bed volume: 6 ml; Pharmacia AB). The column was washed with saline, and then the IgG was eluted with HCl in saline (pH 2.5). The IgG eluted in this manner was confirmed to be pure by sodium dodecyl sulfate-polyacrylamide gel electrophoresis (SDS-PAGE).

B. Identification of IgG Subclasses of MCAs

1. Heavy Chains

The purified MCA solutions were reacted with sheep antisera to human IgG1, IgG2, IgG3, and IgG4 (Serotec Inc.). The subclass of each MCA was identified on the basis of which antisera resulted in formation of an immunoprecipitation ring. It was thus found that No. 86, No. 1, and Sl-1 MCAs reacted only with the anti-IgG1 and did not react with the other three antisera. Therefore, all of these anti-HIV MCAs were identified to be IgG1.

2. Light Chains

A microtiter plate was coated with goat antibody to human IgG (Tago Inc.). Each of the purified MCAs was then reacted with this anti-human IgG-coated plate. Next, in accordance with the method for ELISA described earlier in section B of Experimental Example 1, alkaline phosphatase-conjugated goat antibodies to human lambda chain and to kappa chain (Tago Inc.) were employed and the type of each MCA was identified. As a result, No. 86 MCA was shown to have a kappa chain, while No. 1 MCA and Sl-1 MCA were found to have lambda chains.

C. Vital Antigens Recognized by the MCAs

The Western blot method (Bio Rad Immunoblot Assay; Bio Rad Inc.)was employed to identify which vital antigens were recognized by MCAs No. 86 and No. 1. MCA No. 1 has also been referred to as MCA 1.2 by the inventors; thus, MCA 1 and MCA 1.2 refer to the same cell line. The procedures of the assay technique are briefly described as follows.

The HTLV-III strain of HIV was applied to SDS-PAGE, the separated viral antigens were blotted on nitrocellulose strips, and each of the semi-purified MCAs was reacted thereon. Next, peroxidase-conjugated antibody to human IgG was reacted with the strips, and finally, to develop color, an enzyme substrate was reacted with the strips. The results are shown in FIG. 1. In the figure, A is serum from an AIDS patient, B is serum from a normal human, C is No. 86, D to G are subclones of No. 86, H is the clone of No. 1, and I is Sl-1.

MCA No. 86 reacted strongly with gp41 and reacted weakly with gp120. As the reason for reacting with both gp41 and gp120, it is possible that MCA No. 86 was a mixture of one MCA which reacted with gp41 and another MCA which reacted with gp120. To investigate this possibility, the hybridoma producing MCA No. 86 was again cloned, yielding subclones 1, 2, 3, and 4, and the-MCA produced-by each of those subclones was also subjected to the Western blot assay. As seen in D, E, F, and G, the MCA from each of the 4 subclones of hybridoma No. 86 reacted with both gp41 and gp120. This finding suggests that MCA No. 86 either recognizes an antigenic epitope which is present on both gp41 and gp120, or is an antibody directed at the cleavage site of gp41 and gp120. MCA No. 86 also reacted with gp160, and the reason for this is that this antigen is a glycoprotein constructed from gp41 and gp120.

MCA No. 1 reacted with gp120. It, of course, also reacted with gp160, which is the precursor of gp120.

MCA Sl-1 did not react with any antigen on Western Blotted paper.

D. Radioimmunoprecipitation assay (RIPA)

It sometimes occurs that some antigenic determinants recognized by MCAs are not detected by the Western blot analysis. This is thought to be due to the destruction of tertiary structure of antigens by strong detergent, heat, and methanol treatment of antigens used in the Western blot assay. This phenomenon was observed in the case of MCA Sl-1. Therefore, the antigens recognized by MCA Sl-1 was determined by RIPA as follows.

$^{35}$S labeled cell extracts for RIPA were prepared as follows. MOT cells or HTLV. IIIb infected MOT cells (4 days after infection the MOT was equal to $10^3$ TCID$_{50/5 \times 10^6}$ cells) were labeled with $^{35}$S-cysteine and $^{35}$S-methionine (50 $\mu$Ci/ml total activity). The labeling media was RPMI 1640 containing 1/10 the normal concentration of methionine, 10% extensively dialized fetal calf serum, the other essential amino acids and the $^{35}$S labeled amino acids. Uninfected and infected MOT cells were cultured 14 hours in the labeling media and then washed with PBS(−). After washing, the cells were lysed with RIPA buffer (20 mM Tris-HCl pH 7.4, 1% Deoxycholate, 1% Triton X-100, 0.1% Sodium Dodecxysulfate and 1 mM (p-Amidinophenyl)methanesulfonyl fluoride). The lysate was clarified by high speed centrifugation (18,000 rpm, 60 minutes) at 4° C. The labeled antigens were divided and treated with 20 or 100 mM dithiothreitol (DTT) at 37° C. for 30 or 60 minutes or incubated in the absence of DTT for 30 or 60 minutes. The labeled antigens were immunoprecipitated by the MCA Sl-1 and HIV+human serum antibodies conjugated to protein-A sepharose beads in the presence of RIPA buffer.

Figure 2:
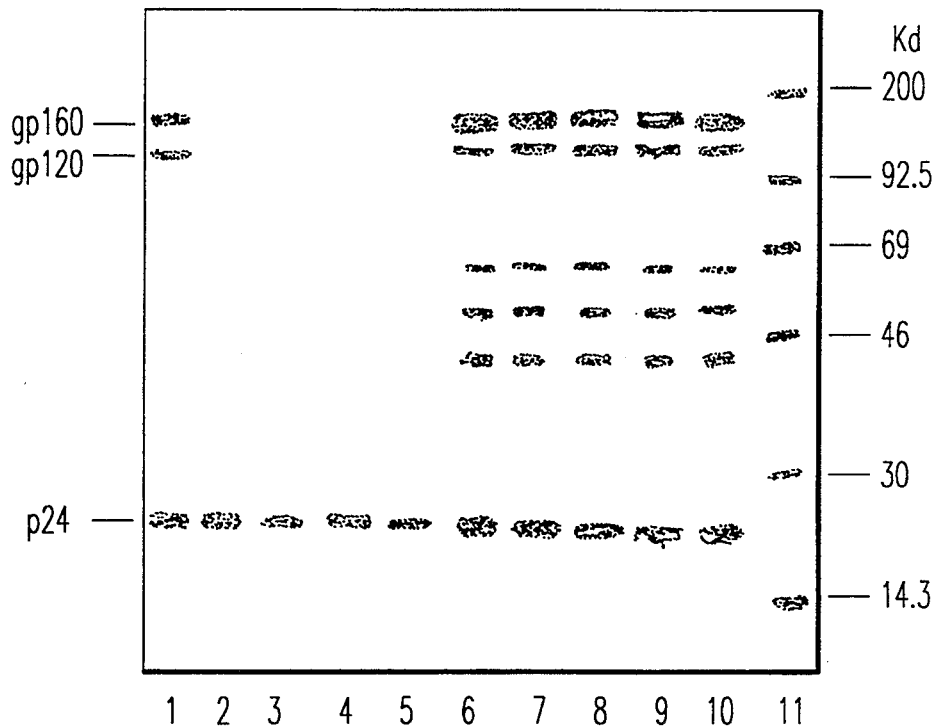
FIGS. 2, 3, and 4 illustrate the results of radioimmunoprecipitation assays to determine the antigenic determinants recognized by MCA Sl-1
Figure 3:
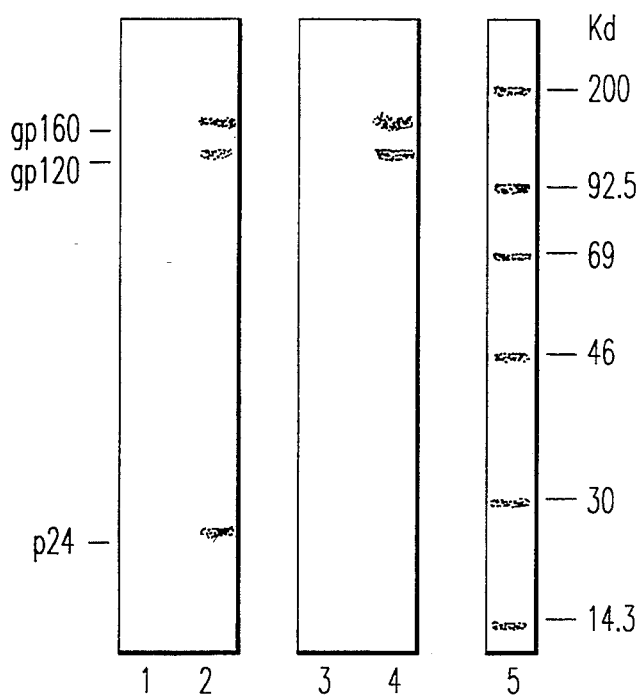
Figure 4:
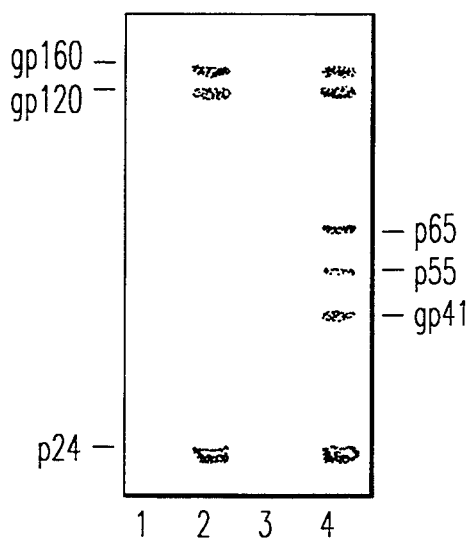

Labeled antigen-antibody complex conjugated to protein A-sepharose beads were washed eight times with RIPA buffer, twice with 10 mM Tris HCl pH 6.8, and then suspended in sample buffer (62.5 mM Tris HCl pH 6.8, 1% SDS, 20% glycerol, 0.2% bromphenol blue) in the presence or absence of 2% 2-mercaptoethanol. After heating the suspension at 100° C. for 3 minutes, released labeled antigens were separated on a 10% acrylamide gel. After electrophoresis, the gel was fixed with 50% methanol-10% acetic acid, immersed in 1M salicylic acid - 3% glycerol, and dried using gel drier. The dried gel was autoradiographed at −80° C. for 3 to 5 days. From FIGS. 2, 3, and 4, the following results were obtained:

(1) MCA Sl-1 recognizes gp 120.
(2) The antigenic determinant on gp120 (gp160) was easily destroyed by sulfhydryl reagents.

E. Binding to Surface of HIV-Infected Cells

The ability of MCAs No. 86, No. 1, and Sl-1 to bind to the surface of HIV-infected cells was investigated by the indirect fluorescent antibody technique.

MOT cells (an HTLV-II transformed cell line), $5 \times 10^6$ cells, were mixed with $2.5 \times 10^6$ TCID$_{50}$ of HTLVIIIb, and this mixture was incubated at 37° C. for 2 hr to permit infection to proceed. These cells were then cultured for 3 days in RPMI 1640 medium containing 10% FCS, after which the cells were washed 3 times at 4° C. with PBS containing 0.1% NaN$_3$. As, the negative control, MOT cells which were not infected with HIV were employed.

These unfixed, cells were dispensed into conical tubes to give $2 \times 10^6$ cells/tube, and centrifugation was performed at 1,500 rpm for 5 minutes. The supernatant was discarded, and the cell pellet was suspended in 100 $\mu$l of 50 $\mu$g/ml MCA in 0.1% NaN$_3$-HBSS. This suspension was reacted at 4° C. for 60 minutes, and then the cells were washed 3 times with 0.1% NaN$_3$-1 mM EDTA-PBS. Each cell pellet was suspended in 100 $\mu$l of fluorescein isothiocyanate-labeled antibody to human IgG (50×dilution; Tago Inc.), followed by reaction at 4° C. for 60 minutes.

The cells treated as described above were next analyzed by flow cytometry (FAC Scan; Becton Dickinson, Co.). The status of binding was investigated for the following combinations: HTLV-IIIb-infected MOT cells and serum (100×diluted) from an AIDS patient, uninfected MOT cells and serum (100×diluted) from an AIDS patient, HTLV-IIIb-infected MOT cells and MCA Sl-1 uninfected MOT cells and MCA Sl-1, HTLV-IIIb-infected MOT cells and MCA V1, and uninfected MOT cells and MCA V1. V1 was an IgG human MCA specific for an irrelevant antigen.

Figure 5A:
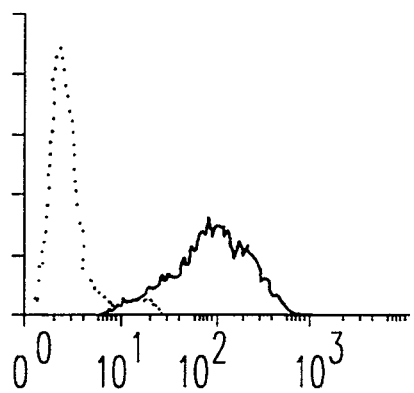
FIG. 5A–5C illustrates the results of indirect fluorescent antibody assays to determine the ability of MCA Sl-1 to bind to the surface of HIV-infected cells.
Figure 5B:
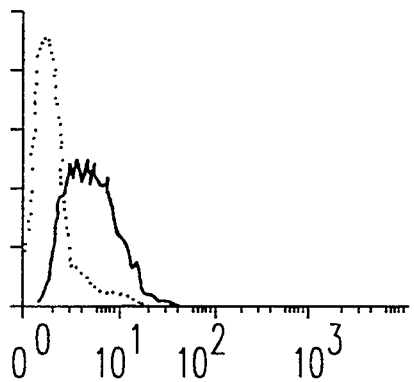
Figure 5C:
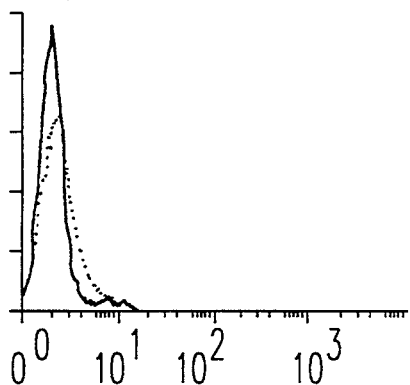

The following results were obtained. MCA Sl-1 bound to the surface of HIV-infected cells, but it did not bind to the uninfected cells. The same results were Obtained with MCA No. 86 and MCA No. 1. MCA V1, which was not specific for HIV, did not react with the HIV-infected cells (FIG. 5).

With an MCA which reacts with the surface of virus-infected cells, it can be speculated that it might be possible to destroy the infected cells in the presence of complement or in the presence of lymphocytes or macrophages, thereby stopping the production of new virus and permitting suppression of the spread of the infection.

F. Neutralization assay

The neutralizing assay of the MCAs was performed by two methods: neutral red dye uptake and p24 antigen capture. The neutral red dye uptake neutralization assay is based on the following premise: when HIV infects permissive cells, the cells lyse after a short time. Neutral red dye is incorporated into the cytoplasm of viable cells. In the neutral red dye uptake neutralization assay, if a MCA could bind to HIV and prevents it from entering permissive cells, the cells-would remain viable and they would take up neutral red dye, giving a colorimetric indication of cell survival which would be indicative of the neutralization of HIV. The protocol is given below.

Protocol for Neutralization Assay: Neutral Red Dye Uptake

Figure 6:
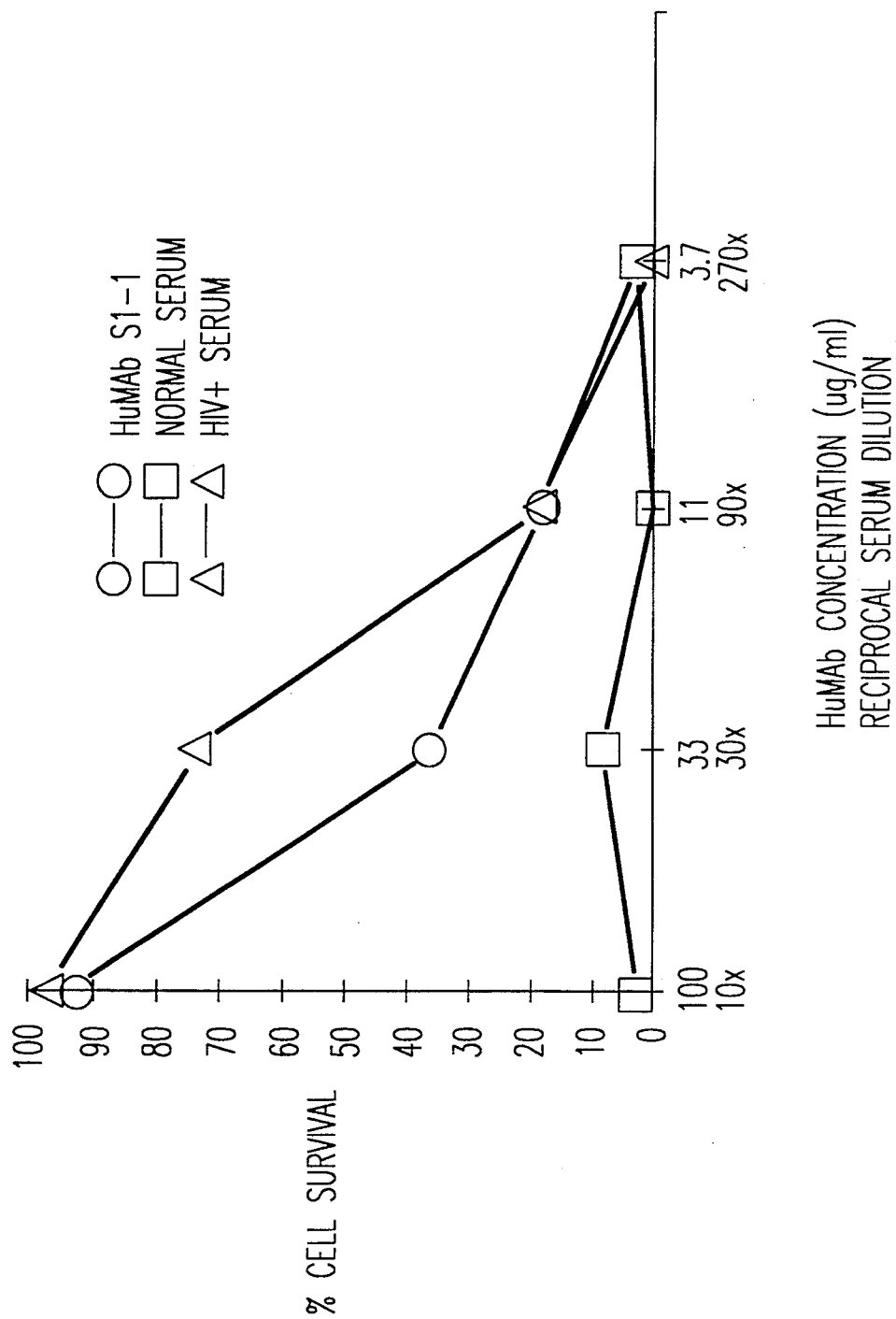
FIG. 6 illustrates the results of a neutral red dye uptake assay to determine the ability of MCA Sl-1 to neutralize HIV-IIIb.

Supernatant from HTLV-IIIb infected H9 cells was used as a virus source for the neutralization assays. A Multiplicity of Infection (MOI) of 20–25 was mixed with dilutions of anti-HIV antibody and incubated for 1 hour at 37° C. HIV mixed with an irrelevant MCA or HIV mixed with HIV positive serum were used as controls. After the virus-antibody incubation, a CD4+cell line (MOT) was added at $3 \times 10^4$ cells/well. These plates, containing HIV, antibody, and MOT cells were then incubated for either 5 or 6 days. On day 5 or 6, the cells in the 96-well microtiter plates were suspended by micropipette action and 100 $\mu$l was transferred into corresponding wells of a poly-L lysine coated plate containing 100 μl of 0.014% neutral red dye in media. The neutral red dye containing plates were incubated for 1 hour at 37° C. All the cells attach to the poly-L lysine on the bottom of the well while only the viable, undamaged cells took up the neutral red dye. After 1 hour, the plate was washed free of excess dye and 100 μl of 1% acetic acid in 70% ethanol was then added to the 96-well plates, The cells containing the dye lysed and released the dye into the supernatant, A colorimetric determination of cell survival was made using a Titertek ELISA reader at 540 nm, Results: Neutral Red Dye Uptake The following results were obtained in the neutral red dye uptake neutralization assay. MCA Sl-1 was observed to neutralize over 90% of the infectious HIV at a concentration of 100 μg/ml as measured by the neutral red dye uptake, cell survival assay (FIG. 6). As the concentration of MCA Sl-1 decreased, it inhibited less HIV from infecting the permissive cell line, MOT. Normal serum did not inhibit HIV infection at all, while HIV-positive serum inhibited HIV infection to a 90-fold dilution. Neither MCA Sl-1 nor HIV-positive serum effectively neutralized HIV at concentrations less than 11 μg/ml or at greater than 90-fold dilutions, respectively.

Protocol for Neutralization Assay Antigen capture Assay

Another HIV neutralization assay was performed that detects the p24 HIV core protein in an ELISA antigen capture assay. When HIV infects permissive cells, it replicates itself inside the cell and releases vital particles from the cell into the surrounding supernatant where they can be detected. Again, if a MCA were to bind to HIV and inhibit penetration into the cell, HIV could not replicate itself and would not release viral particles into the supernatant. This p24 antigen capture was performed as follows.

Cell-free HTLV-IIIb infected H9 supernatant at a MOI of 20–25 was incubated with dilutions of anti-HIV antibody in 96-well microtiter plates for 1 hour at 37° C. It is important to note that the amount of HIV inoculum could not be detected by this antigen capture assay. Only the viral particles produced by HIV infected cells are detected. HIV mixed with an irrelevant MCA or HIV mixed with HIV-positive sera were used as controls. After the virus-antibody incubation, a CD4+ cell line (MOT) was added to the plates at $3 \times 10^4$ cells/well. These plates containing HIV, antibody, and MoT cells were then incubated for 7 days. Samples of the supernatants were taken from each well at 3, 5, and/or 7 days. These samples were heat-inactivated for hour at 56° C. and then added to 96-well ELISA plates coated with 5 μg/ml of HIV-positive serum. After 1 hour incubation at room temperature, the ELISA plates were washed with 0.05% Tween-20 in phosphate buffered saline. Then a biotinylated MCA specific for p24 (Western Blot) was added to the plates at 2 μg/ml, and the plate was incubated and washed as before. Streptavidin conjugated alkaline phosphatase was then added to the plate at a concentration of 1 μg/ml, incubated for 1 hour and washed free of excess reagent. One mg/ml of para-nitrophenyl phosphate in carbonate buffer pH 9.5 was added to the plate and the optical densities of the wells were read on a Titertek Multiskan ELISA reader at 405 nm. An increase in optical density indicated that more p24 was present in the original culture supernatant.

Results: p24 Antigen Capture

Figure 7:
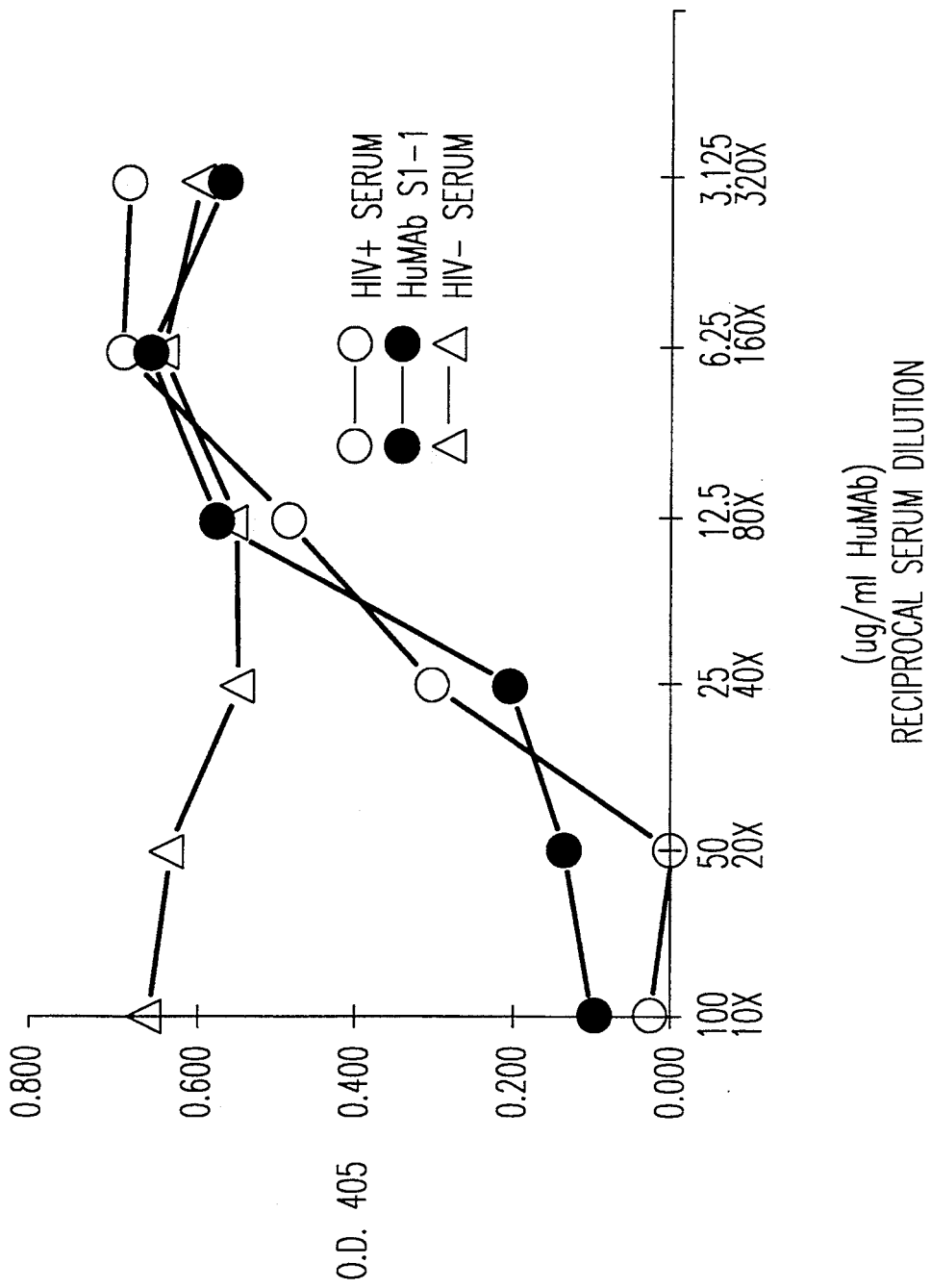
FIG. 7 illustrates the results of an antigen capture assay to determine the ability of MCA Sl-1 to neutralize HTLV-IIIb.

The following results were obtained from the HIV p24 antigen capture neutralization assay. MCA Sl-1 blocked HIV infection significantly as evidenced by low levels of the p24 HIV core protein in the presence of Sl-1 concentrations of from 100 to 25 μg/ml (FIG. 7). Sl-1 did not maintain neutralization at lower concentrations. HIV-positive serum completely neutralized infection at 10-fold and 20-fold dilutions and partially neutralized HIV at a 40-fold dilution, but also did not maintain neutralization at higher dilutions as indicated by high levels of p24.

Discussion

MCA Sl-1 neutralizes HIV infection in permissible cells. The degree of neutralization depends on the concentration of the MCA. At high concentrations (100 μg/ml) Sl-1 inhibits 93% of cell-free HIV from infecting cells in a cell survival assay. Although Sl-1 lost the capacity to neutralize HIV at lower concentrations, HIV-positive serum also lost the ability to neutralize at high dilutions. Consistent with the cell survival assay results, less p24 HIV core protein was produced in the presence of Sl-1, indicating that Sl-1 inhibits HIV infection.

The results of the various experiments described above are compiled in the following Table 2.

TABLE 2

| Property | No. 86 | No. 1 | Sl-1 |
|---|---|---|---|
| Isotype of MCA | IgG1.κ | IgG1.λ | IgG1.λ |
| Binding to HIV in ELISA | HTLV-IIIb CR10/N1T | HTLV-IIIb CR10/N1T | HTLV-IIIb CR10/N1T |
| Binding to HTLV-IIIb infected cells | | | |
| fixed | + | + | + |
| unfixed | + | + | + |
| Viral antigens recognized by MCA | gp120 gp41 | gp120 | gp120 |
| Neutralization | − | − | + (90% at 100 μg/ml dye uptake method) |
| MCA production rate (μg/$10^6$ cells/day) | 10 | 20 | 5 |

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by letters patent of the United States is:

1. A hybridoma having all of the identifying characteristics of ATCC accession no. HB10074.

2. A human monoclonal IgG1 antibody produced by the hybridoma of claim 1.

3. The hybridoma having ATCC accession no. HB 10074.

* * * * *